US008273380B1

(12) United States Patent  
Gall-Krasnick

(10) Patent No.: US 8,273,380 B1  
(45) Date of Patent: Sep. 25, 2012

(54) FORTIFIED BEVERAGE FOR MINIMIZING AND/OR PREVENTING JET LAG

(75) Inventor: Andrea Gall-Krasnick, Kailua, HI (US)

(73) Assignee: Jetway Inc., Kailua, HI (US)

( * ) Notice: Subject to any disclaimer, the term of this patent is extended or adjusted under 35 U.S.C. 154(b) by 473 days.

(21) Appl. No.: 12/468,765

(22) Filed: May 19, 2009

(51) Int. Cl.
*A61K 31/44* (2006.01)
*A61K 31/4415* (2006.01)
*A61K 31/714* (2006.01)
*A61K 31/07* (2006.01)
*A61K 31/195* (2006.01)
*A61K 31/59* (2006.01)
*A61K 31/592* (2006.01)
*A61K 31/593* (2006.01)
*A61K 33/00* (2006.01)
*A61K 33/16* (2006.01)
*A61K 36/258* (2006.01)
*A61K 36/28* (2006.01)

(52) U.S. Cl. ........ 424/639; 424/640; 424/643; 424/667; 424/670; 424/678; 424/679; 424/682; 424/683; 424/692; 424/693; 424/722; 424/728; 424/737; 424/752; 424/766; 514/52; 514/167; 514/168; 514/355; 514/563; 514/725; 514/729; 514/763

(58) Field of Classification Search .................. 424/639, 424/643, 667, 678, 682, 728, 737, 752, 766, 424/640, 670, 679, 683, 692, 693, 722; 514/52, 514/167, 168, 355, 563, 725, 729, 763
See application file for complete search history.

(56) References Cited

U.S. PATENT DOCUMENTS

| | | | |
|---|---|---|---|
| 4,448,770 A | 5/1984 | Epting, Jr. | |
| 4,592,909 A | 6/1986 | Winer et al. | |
| 4,600,723 A | 7/1986 | Short et al. | |
| 4,786,510 A | 11/1988 | Nakel et al. | |
| 4,858,609 A | 8/1989 | Cole | |
| 4,901,296 A | 2/1990 | Mitchell | |
| 4,992,282 A | 2/1991 | Mehansho et al. | |
| 5,006,985 A | 4/1991 | Ehret et al. | |
| 5,114,723 A | 5/1992 | Stray-Gundersen | |
| 5,240,732 A | 8/1993 | Ueda | |
| 5,397,786 A | 3/1995 | Simone | |
| 5,402,190 A | 3/1995 | Waldman | |
| 5,567,424 A | 10/1996 | Hastings | |
| 5,597,585 A | 1/1997 | Williams et al. | |
| 5,770,217 A | 6/1998 | Kutilek, III et al. | |
| 6,265,450 B1 | 7/2001 | Asami et al. | |
| 6,596,301 B1 | 7/2003 | Masuyama et al. | |
| 7,090,878 B2 | 8/2006 | Mehansho et al. | |
| 7,112,343 B1 | 9/2006 | Shoemake | |
| 7,115,297 B2 | 10/2006 | Stillman | |
| 7,160,565 B2 | 1/2007 | Rifkin | |
| 7,632,532 B2 * | 12/2009 | McKee et al. ................ | 426/548 |
| 2003/0008048 A1 * | 1/2003 | Winston et al. ............. | 426/548 |
| 2003/0152652 A1 * | 8/2003 | Baker et al. ................. | 424/737 |
| 2003/0203072 A1 | 10/2003 | O'Mahony et al. | |
| 2004/0062821 A1 | 4/2004 | Avram | |
| 2005/0002178 A1 | 1/2005 | Wu et al. | |
| 2005/0064070 A1 | 3/2005 | Liebrecht | |
| 2005/0177192 A1 | 8/2005 | Rezai et al. | |
| 2005/0253018 A1 | 11/2005 | George, Jr. | |
| 2006/0009822 A1 | 1/2006 | Savage et al. | |
| 2006/0093705 A1 | 5/2006 | Mehansho et al. | |
| 2009/0117224 A1 | 5/2009 | Robergs | |

FOREIGN PATENT DOCUMENTS

WO WO 95/05819 3/1995
WO WO 2007/095605 A2 11/2007

OTHER PUBLICATIONS

Sidneva, E.S. et al., "Effects of vitamin supply on spontaneous and chemically induced mutagenesis in human cells," Bulletin of Experimental Biology and Medicine, vol. 139(2), pp. 230-234 (Feb. 2005).*
Waterhouse, J. et al., "Jet lag: trends and coping strategies," The Lancet, vol. 369, Issue 9567, pp. 1117-1129 (Mar. 2007).*
Haimov, I. et al., "The prevention and treatment of jet lag," Sleep Medicine Review, vol. 3(3), pp. 229-240 (1999).*
Nicholson, A.N., "Sleep and intercontinental flights," Travel Medicine and Infectious Disease, vol. 4, pp. 336-339 (2006).*
Conaglen, P.K., et al. "Effect of melatonin on jet lag after long haul flights", British Medical Journal 1989; 298:705-707.
Gruenwald, J. "The Global Herbs & Botanicals Market: Herbs and botanicals are currently showing the most potential in functional foods and cosmeceuticals". Analyze & Realize ag (A&R) Berlin, Germany Neutraceuticals Word magazine; Apr. 2009. http://www.nutraceuticalsworld.com/articles/2008/07/the-global-herbs-botanicals-market.
MayoClinic.com. 2008 "Jet Lag Disorder" © 1998-2009 Mayo Foundation for Medical Education and Research (MFMER), DS01085, Jul. 11, 2008. http://www.mayoclinic.com/health/jet-lag/DS01085.
Merck Manual Professional, Merck Manuals Online Medical Library "Melatonin: Dietary Supplements" Last revision: Nov. 2005. http://www.merck.com/mmpe/print/sec22/ch331/ch331t.html. U.S. Food and Drug Administration Center for Food Safety and Applied Nutrition (CFSAN) Office of Nutritional Products, Labeling, and Dietary Supplements Sep. 2003. "Claims That Can Be Made for Conventional Foods and Dietary Supplements". http://www.cfsan.fda.gov/DMS/hclaims.html.
World Health Organization. "Traditional Medicine" Fact Sheet N° 134, Revised Dec. 2008.
Mayo Clinic staff, "Jet Lag Disorder", http://www.mayoclinic.com/health/jet-lag/DS01085/DSECTION=causes; pp. 1-6, Jul. 10, 2010.
Professor Martin B. Hocking, et al., Common cold transmission in commercial aircraft: Industry and passenger implications; Professor Martin B. Hocking, Department of Chemistry, University of Victoria, pp. 1-6, May 2004.
Dr. Samuel Strauss: Occs1s@vmmc.org; Jet-Lag & Transmeridian Flight, pp. 1-3.
RITA/BTS/2010 Traffic Data for U.S. Airlines and Foreign Airlines U.S. Flights: Total Passengers up fro . . . ; RITA Research and Innovative Technology Administration Bureau of Transportation Statistics; 2010 Traffic Data for U.S. Airlines and Foreign Airlines U.S. Flights: Total Passenger Up from 2009, Still Below 2008; pp. 1-6, 2010.

* cited by examiner

*Primary Examiner* — John Pak
(74) *Attorney, Agent, or Firm* — Hogan Lovells US LLP

(57) ABSTRACT

A beverage for minimizing or reducing jet lag symptoms preferably includes vitamin B3, vitamin B5, vitamin B6, vitamin B12, vitamin D, zinc, calcium, iodine, magnesium, manganese, ginseng, ginkgo biloba, grape seed extract, *Echinacea* extract and water. A method for minimizing or reducing jet lag symptoms including ingestion of the beverage by a traveler, one hour prior to a flight, and/or during the flight, and/or after a flight.

7 Claims, No Drawings

FORTIFIED BEVERAGE FOR MINIMIZING AND/OR PREVENTING JET LAG

FIELD OF THE INVENTION

The present invention relates to fortified beverages and more particularly to beverages fortified with vitamins, minerals and/or herbs for preventing and/or minimizing jet lag symptoms.

BACKGROUND OF THE INVENTION

Jet lag, also known as jet fatigue and time zone change syndrome, generally results from disruption of circadian rhythms in the human body. It is a temporary condition characterized by various psychological and physiological effects on the human body that occur following long flights through several time zones. It mostly occurs in people traveling east to west or west to east, and less often in those traveling within a single time zone or to a neighboring time zone, such as when one travels north or south. Jet lag affects people of all ages, and although it varies widely from person to person, it tends to become more severe in older travelers.

Jet lag symptoms include but are not limited to, fatigue, insomnia, anxiety, constipation, diarrhea, confusion, dehydration, headache, irritability, nausea, sweating, coordination and circulation problems (including deep vein thrombosis), and even short-term memory loss. Dehydration, which is exacerbated by the lack of humidity in aircraft cabins and by passengers' limited access to water and other liquids, can cause headaches, dry skin and nasal irritation and make travelers more susceptible to any colds, coughs, sore throats and flu that other travelers in the aircraft may have. Some individuals report additional symptoms, such as heartbeat irregularities and an increased susceptibility to illness.

Jet lag symptoms do not always appear immediately. For some travelers, it may be two or three days before any symptoms are noted. Like many sleep disorders, jet lag is not in itself a specific disease or condition; it is a symptom or set of symptoms. It is not characterized as a single disease and there is no known "cure".

Given the prevalence of air travel, jet lag is a significant problem resulting in loss of productivity. It can be a very significant factor for business travelers, athletes, military personnel and recreational travelers (see, WO 2007/095605). Indeed, in one 1994 survey of New Zealand-based international flight attendants, 96% of respondents said they suffered from jet lag despite being accustomed to long haul travel, with 90% suffering from tiredness after arrival, 94% experiencing loss of energy and motivation, and 93% reporting broken sleep after arrival (Winget, C. M., et al. "Review of Human Psychological & Performance Changes Associated with Desynchronosis of Bio Rhythms", *Av Space & Env Med* 1984; 55: 1085-96.). Another survey reported that that the principal symptoms of jet lag are sleepiness and fatigue during the day (suffered by 90%) and inability to sleep at night (suffered by 78%), with 45% of surveyed travelers reporting they were bothered severely.

Most travelers experiencing jet lag do not seek or require treatment. Nonetheless, some medications are used to relieve jet lag symptoms, including (1) nonbenzodiazepines such as zolpidem (Ambien™), eszopiclone (Lunesta™), and zaleplon (Sonata™); and (2) benzodiazepines such as triazolam (Halcion™). These medications may help travelers sleep during their flight—and for several nights afterward. Side effects are uncommon but may include nausea, vomiting, amnesia, sleepwalking, confusion and morning sleepiness. Although these medications appear to help sleep duration and quality, they may not diminish daytime symptoms of jet lag (MayoClinic.com. 2008, "Jet Lag Disorder", © 1998-2009 Mayo Foundation for Medical Education and Research, Jul. 11, 2008.).

There are numerous jet lag remedies such as melatonin which is a synthetic hormone available in pills or patches (see U.S. Pat. No. 6,638,963 and WO 95/05819). While melatonin is a popular jet lag remedy, a standard dosage of this dietary supplement is not established and ranges from 0.05 to 5 mg taken, and may have adverse effects including hangover drowsiness, headache, and transient depression" (Merck Manual Professional, Merck Manuals Online Medical Library "Melatonin: Dietary Supplements" Last revision: November 2005). Side effects have been reported and melatonin is banned for over-the-counter use in Canada, Great Britain, and other European countries.

Other jet lag remedies include hormone therapy such as galanthamine (see U.S. Publication No. 005585375A), pheromone therapy (see WO2007/095605A2), electrical brain stimulation (see U.S. Publication No. 2005/0177192), hand held light therapy, (see U.S. Publication No. 2006/0009822), contact lenses (see U.S. Pat. No. 5,402,190), eye masks (see U.S. Pat. No. 4,858,609), watches (see U.S. Pat. No. 4,901,296), as well as garments (see U.S. Publication No. US2005/0002178), computer systems (see U.S. Pat. No. 5,006,985) and magnetic mats (see U.S. Publication No. 2005/0251038).

Airborne® is a dietary supplement using a proprietary combination of 17 vitamins, minerals and herbs. Airborne® literature asserts that the key ingredients have been shown to help support an individual's immune system as shown in scientific studies and medical journals. This dietary supplement is available in pill, lozenge and powder forms. A container of water, or a water-based delivery medium in which to take the product in or with, is not provided with this product.

Another jet lag product is currently marketed under the name No-Jet-Lag® in chewable 340 mg tablets and is described as containing five homeopathic remedies. It is suggested that tablets be taken two hours before each flight, every two hours during a flight, and two hours after landing. A container of water or a water-based delivery medium in which to take the product in or with, is not provided with this product.

While there is a possibility that ingesting certain vitamins and minerals as part of a daily regimen, or in advance of, or during a flight, may be of some inherent benefit, jet lag symptoms may be exacerbated due to increased dehydration. Moreover, if one considers dissolving certain vitamins and minerals in water to offset such dehydration issues, the resulting solution may not be sufficiently appetizing for complete consumption due to characteristics imparted by such vitamins and minerals. For example, vitamins A and E can create a ring on a bottle and/or an oily film on the beverage, vitamin B1 can taste metallic, vitamin B2 can turn a solution yellow, vitamin C can cause browning and other color changes, zinc and iron can impart a metallic taste, and calcium can cause clouding, solubility and pH issues.

Thus, there remains a need for a remedy for minimizing or preventing jet lag symptoms.

SUMMARY OF THE INVENTION

A beverage of the present invention for preventing and/or minimizing jet lag symptoms preferably includes an aqueous solution, dispersion, suspension or other aqueous form, of Vitamin B3, Vitamin B5, Vitamin B6, Vitamin B12, Vitamin D, zinc, calcium, iodine, magnesium, manganese, ginseng, ginkgo biloba, grape seed extract and an *Echinacea* extract. The beverage preferably includes, for each 8 fluid ounces thereof, at least 20 mg of vitamin B3, at least 10 mg of vitamin B5, at least 2 mg of vitamin B6, at least 6 µg of vitamin B12, and at least 20 mg of vitamin D. The beverage may include, for each 8 fluid ounces of the beverage, at least 1.5 mg of zinc, at least 100 mg of calcium, at least 37.5 µg of iodine, at least 7.5 mg of magnesium, and at least 2 mg of manganese. The beverage may also include, for each 8 fluid ounces of the beverage, at least 50 mg of ginseng, at least 50 mg of ginkgo biloba, at least 50 mg of grape seed extract, and at least 100 mg of *Echinacea* extract.

In other preferred embodiments, for each 8 fluid ounces, the beverage may include 2-40 mg of vitamin B3, 2-20 mg of vitamin B5, 1-5 mg vitamin B6, 2-24 µg of vitamin B12, 4-400 mg vitamin D, 0.5-5 mg zinc, 20-200 mg of calcium, 20-100 µg of iodine, 2-20 µg of potassium, 5-50 mg of magnesium, 1-5 mg manganese, 50 mg ginseng, 5-100 mg of ginkgo biloba, 5-100 mg of grape seed extract and/or 10-200 mg of *Echinacea* extract. Another embodiment of the inventive beverage for minimizing or reducing jet lag symptoms includes (a) water, (b) at least 4 vitamins selected from the group consisting of vitamin A, vitamin B1, vitamin B2, vitamin B3, vitamin B5, vitamin B6, vitamin B12, vitamin C, and vitamin D, (c) at least 5 minerals selected from the group consisting of zinc, calcium, iodine, potassium, magnesium, manganese, and selenium; and (d) at least 4 herbs selected from the group consisting of American ginseng, Korean ginseng, Siberian ginseng, ginkgo biloba, grape seed extract, goldenseal, *Echinacea* extract, chamomile, and water. A method of minimizing or reducing jet lag symptoms, comprising ingesting at least 8 fluid ounces of any of the aforementioned beverages at least one hour before a flight, during a flight, and/or after a flight.

DETAILED DESCRIPTION OF PREFERRED EMBODIMENTS

A beverage of the present invention for preventing and/or minimizing jet lag symptoms preferably includes an aqueous solution, dispersion, suspension or other aqueous form, of Vitamin B3, Vitamin B5, Vitamin B6, Vitamin B12, Vitamin D, zinc, calcium, iodine, magnesium, manganese, ginseng, ginkgo biloba, grape seed extract and an *Echinacea* extract. A beverage preferably includes, for each 8 fluid ounces thereof, at least 20 mg of vitamin B3, at least 10 mg of vitamin B5, at least 2 mg of vitamin B6, at least 6 µg of vitamin B12, and at least 20 mg of vitamin D. The beverage may include, for each 8 fluid ounces, at least 1.5 mg zinc, at least 100 mg of calcium, at least 37.5 µg of iodine, at least 7.5 mg of magnesium, and at least 2 mg of manganese. The beverage may also include, for each 8 fluid ounces, at least 50 mg of ginseng, at least 50 mg of ginkgo biloba, at least 50 mg of grape seed extract, and at least 100 mg of *Echinacea* extract. In other preferred embodiments, for each 8 fluid ounces, the beverage may include 2-40 mg of vitamin B3, 2-20 mg of vitamin B5, 1-5 mg vitamin B6, 2-24 µg of vitamin B12, 4-400 mg vitamin D, 0.5-5 mg zinc, 20-200 mg of calcium, 20-100 µg of iodine, 5-50 mg of magnesium, 1-5 mg manganese, 5-100 mg ginseng, 5-100 mg of ginkgo biloba, 5-100 mg of grape seed extract and/or 10-200 mg of *Echinacea* extract.

Non-flavoring ingredients may include ethyl alcohol and propylene glycol.

Another embodiment of the inventive beverage for minimizing or reducing jet lag symptoms includes (a) water, (b) at least 4 vitamins selected from the group consisting of vitamin A, vitamin B1, vitamin B2, vitamin B3, vitamin B5, vitamin B6, vitamin B12, vitamin C, and vitamin D, (c) at least 4 minerals selected from the group consisting of zinc, calcium, iodine, magnesium, manganese, and selenium, and (d) at least four herbs selected from the group consisting of American ginseng, Korean ginseng, Siberian ginseng, ginkgo biloba, grape seed extract, goldenseal, *Echinacea purpurea*, *Echinacea pallida*, chamomile.

It should be understood that although the preferred beverages are characterized as an aqueous solution, one or more of the ingredients may be in suspension, in a dispersion, in an emulsion, in a complex, or in some other form in a water-based beverage, and the term aqueous solution as used herein is intended to encompass all such compositions and forms of the beverages of the present invention described herein.

It should also be understood that although the preferred beverages and ingredients are described in terms of an 8 fluid ounce serving, that the preferred amounts of the recited constituents which are expressed in terms of an 8 fluid ounce serving, are intended to encompass smaller and larger servings having the same ratio or relative range of constituents. So, for example, if a preferred embodiment ingredient is expressed herein as being present in an 8 fluid ounce serving in an amount of at least 40 mg, then for a 12 fluid ounce serving of the beverage, for example, at least 60 mg of the constituent would be required to be present.

Many of the preferred ingredients are available in different forms for inclusion in the beverages of the present invention. In addition, for many of the vitamins and minerals of the beverages of the present invention, U.S. recommended daily allowances (USRDA) are established and whenever taste and solubility allow, a full USRDA of each such ingredient is preferably used. Preferred amounts and ingredient forms for inclusion in an 8 fluid ounce aqueous beverage of the present invention are summarized below:

| Constituent | Preferred source | Preferred amount of constituent | Acceptable amount |
|---|---|---|---|
| Vitamin B3 | Niacin (niacinamide) | 20 mg | 2-40 mg |
| Vitamin B5 | Pantothentic acid (calcium pantothenate) | 10 mg | 2-20 mg |
| Vitamin B6 | Pyridoxine HCl | 6 µg | 2-24 µg |
| Vitamin B12 | Cyanocoba Mamen | 6 µg | 2-24 µg |
| Vitamin D | Vitamin D3 | 20 µg | 4-400 µg |
| Zinc | Zinc sulfate | 1.5 mg | 1-5 mg |
| Calcium | Calcium lactate | 100 mg | 20-200 mg |
| Iodine | Potassium iodide | 37.5 µg | 20-300 µg |
| Potassium | Monopotassium phosphate | 5 mg | 2-20 mg |
| Magnesium | Magnesium oxide | 7.5 mg | 5-50 mg |
| Manganese | Manganese sulfate | 2 mg | 1-5 mg |
| *Ginseng* | | 50 mg | 5-100 mg |
| *Ginkgo biloba* | | 50 mg | 5-100 mg |
| Grape seed extract | | 50 mg | 5-100 mg |
| *Echinacea* extract | *Echinacea purpurea* and/or *Echinacea pallida* | 100 mg | 10-200 mg |

µg = micrograms
IU = international units
mg = milligrams

The preferred liquid in which the above ingredients are solubilized is distilled water. Alternatively, spring water, other treated waters, and brewed or powdered tea are also preferred. Acceptable beverage forms in which the above ingredients are solubilized also include fruit and vegetable juices (including lemonade, limeade, orangeade), milk and soy drinks, sodas, colas and ales.

Preferably, the *Echinacea* extract includes extracts from both *Echinacea purpurea* and *Echinacea pallida*. Most preferably, at least 50 mg of each such extract is present in an 8 fluid ounce serving of the beverage.

In an alternate embodiment, the beverage of the present invention may also include selenium, in a preferred amount of at least 55 μg per 8 fluid ounce serving.

In another alternate embodiment of the present invention, substitutions for, or in addition to one or more of the Vitamins B3, B5, B6, and B12 include Vitamin B1 (thiamin), Vitamin B2 (riboflavin), Vitamin C (ascorbic acid), and Vitamin A (palmitate). Acceptable ranges and preferred amounts are as summarized in Tables 4-6 below.

Most preferably to minimize or prevent symptoms of jet lag, travelers flying from east to west, or west to east, should plan to consume an 8 fluid ounce serving of the beverage of the present invention prior to a flight of 3 hours or more. Alternatively, or in addition to a pre-flight beverage, it is most preferred that a second 8 fluid ounce serving of the beverage be consumed during the first half of the flight. Alternatively, or in addition to consumption of a pre-flight and early flight beverage of the present invention, consumption of an 8 fluid ounce serving of the beverage in the last hour of the flight is also suggested. Alternatively, or in addition to consumption of a pre-flight or in-flight beverage of the present invention, consumption of an 8 fluid ounce serving of the beverage after the flight also suggested.

A preferred method of making a beverage of the present invention is to use a hot-fill process (process involving temperatures ranging from 180° to 192° F.), which is a common method of pasteurization known among beverage production facilities for ready-to-drink beverages and other products. Generally, hot filling involves filling containers immediately after the bottle has been through a thermal processing step; it is a method beverage makers use to reduce the chances of potential bacteria in products.

Preferably, a method for combining the ingredients for a beverage of the present invention, in a fortified water format, generally, the process is as follows: a) add hot water to batching tank, b) add sodium citrate and mix thoroughly, c) add vitamin and mineral dry blend and mix thoroughly, d) add herbal blend and mix thoroughly, e) add sucralose and mix thoroughly, f) add acids and mix thoroughly g) add flavors and mix thoroughly, h) heat entire batch to 85° C., i) bottle the pasteurized product, and j) submerge bottles in a cold water bath.

Preferably, a method for combining the ingredients for a beverage of the present invention, in a fortified tea format, generally, the process is as follows: a) add hot water to batching tank, b) add sodium hexametaphosphate and mix thoroughly, c) add teas (black, green, white or red) and mix thoroughly, d) add vitamin and mineral dry blend and mix thoroughly, e) add vitamin C and mix thoroughly, f) add herbal blend and mix thoroughly, g) add sucralose and mix thoroughly, h) add acids and mix thoroughly, i) add flavors and mix thoroughly, j) add colors and mix thoroughly, k) heat entire batch to 85° C., l) bottle the pasteurized product, and m) submerge bottles in a cold water bath.

An alternate method of preparing the beverage of the present invention is an aseptic filling process (also known as cold aseptic, sterile, beverage-sterile, and ultra-clean process) which is also a common method of bottling known among beverage production facilities mostly used for ready-to-drink juice, milk or tea beverages and other products. Generally, the aseptic filling process involves filling a product at ambient (room) temperatures without using any preservatives or cold sterilizing agents, in such a way that it attains a specified shelf-life.

Optimal storage conditions for the present invention are in 40° to 60° F. in a closed atmosphere. The present invention should not be stored in temperatures that exceed 75° F., and should not be exposed to direct sunlight or prolonged heat.

The ingredients in an aqueous solution are marketed in sealed bottles, preferably comprising individual serving sizes of 8 fluid ounces, 12 fluid ounces or 16.9 fluid ounces. Alternatively, a dry mixture of the vitamin/mineral/herb composition that is ready-to-use, in a sealed packet, for mixing in an aqueous liquid by an individual just prior to consumption is contemplated. In yet another form, a dry mixture of the vitamin/mineral/herb composition that is dropped from the interior of a bottle closure and combined with a liquid base (i.e. water or tea) is also one alternative use contemplated.

The vitamins and minerals which are included in the embodiments of the beverages of the present invention for preventing or minimizing jet lag symptoms are Generally Recognized as Safe (GRAS) by the U.S. Food and Drug Administration, and are grandfathered into the Dietary Supplement Health and Education Act of 1994 as widely accepted supplemental dietary items. While each individual constituent of the beverages of the present invention is reported as having a beneficial effect on body functions which manifest jet lag symptoms, the beverages of the present invention at the recommended amounts are expected to minimize and even prevent jet lag beyond what is expected individually for the individual constituents. The reported potential benefits of the individual constituents (either preferred or substituted) of the beverages of the present invention are summarized below in Table 1 for vitamins, in Table 2 for minerals, and in Table 3 for herbs.

TABLE 1

| JET LAG BEVERAGE VITAMINS | |
|---|---|
| Vitamin | Health Benefits as They Relate to Jet Lag Symptoms |
| Vitamin A[1] Palmitate | Boosts immune system (in relation to colds, coughs, sore throats and flu) |
| | Builds resistance to respiratory infections (in relation to colds, etc.) |
| | Improves vision, including night blindness (stress on eyes cause tiredness and headaches) |
| | Assists in growth and repair of body cells (maintenance of body functions) |
| | Helps keep eyes healthy and able to adjust to dim light |
| | Helps keep skin healthy |
| | Helps keep lining of mouth, nose, throat and digestive tract healthy and resistant to infection |
| Vitamin B1[1] (Thiamin) Thiamin HCl | Protects against metabolic imbalances caused by alcohol |
| | Improves mental ability |
| | Beneficial in treatment of heart disease (maintains good circulation) |
| | Helpful treating anemia (counteracts fatigue in persons with low iron) |
| | Useful in neurological disorders (reduces anxiety/nervousness) |
| | Helps body cells obtain energy from food |
| | Helps keep nerves healthy |
| | Promotes good appetite and digestion |
| Vitamin B2[1] (Riboflavin) | Protects exercisers from antioxidant damage (maintain body functions) |
| | Promotes normal growth and development (maintenance of body functions) |
| | Boosts athletic performance |
| | Protects against anemia (counteracts fatigue in persons with low iron) |

TABLE 1-continued

JET LAG BEVERAGE VITAMINS

| Vitamin | Health Benefits as They Relate to Jet Lag Symptoms |
|---|---|
| Vitamin B3[1] (niacin) | Helps cells use oxygen to release energy from food<br>Helps keep eyes healthy and vision clear<br>Helps keep skin around mouth and nose healthy<br>Maintains normal function of the skin, tongue, nervous system, and digestive system<br>Protects against and detoxifies pollutants, alcohol and narcotics<br>Relieves migraine headache<br>Lowers cholesterol and protects against cardiovascular disease<br>May reduce high blood pressure (maintains good circulation) |
| Vitamin B5 (pantothenic acid[1]) d-calcium pantothenate | Helps cells use oxygen to release energy from food<br>Helps prevent fatigue (maintains good circulation)<br>Detoxifies alcohol<br>Helps fight infection by building antibodies (maintains good circulation)<br>Lowers cholesterol; protects against cardiovascular disease (maintains good circulation)<br>Vital for proper functioning of adrenal glands (maintains good circulation)<br>Alleviates arthritis (maintains good circulation)<br>Aids in the metabolism of fat<br>Aids in the formation of cholesterol and hormones |
| Vitamin B6[1] pyridoxine HCl | Boosts the immune system (in relation to colds, etc.)<br>Helps reduce stress<br>Helps normal function of the brain<br>Relieves symptoms of Pre-Menstrual Syndrome (relieves anxiety, fatigue, irritability)<br>Protects against metabolic imbalances<br>Helps assimilate carbohydrates, proteins and fats (maintains proper digestion)<br>Protects against nervous disorders (relieves anxiety, stress)<br>Needed to help nervous tissues function normally<br>Helps to maintain the health of the skin and red blood cells<br>Assists in the metabolism of proteins, carbohydrates, and fats |
| Vitamin B12[1] cyanocoba mamen | Energizes the body<br>Relieves indigestion (refers to any number of gastrointestinal complaints, which can include gas, belching, flatulence, or bloating and upset stomach)<br>Alleviates neuropsychiatric disorders; prevents mental deterioration (relieves anxiety)<br>Protects against toxins and allergens<br>Necessary in the development of normal growth<br>Helps protect against pernicious anemia<br>Protects against night blindness, psoriasis, problems related to menopause, and general malaise (relieves fatigue, irritability) |
| Vitamin C[1] ascorbic acid | Boosts immune system (in relation to colds, etc.)<br>Protects against smoking and various pollutants (provides antioxidants)<br>Necessary for proper functioning of the brain and nerves<br>Encourages iron absorption (counteracts fatigue in persons w/low iron)<br>Combats cardiovascular disease (maintains good circulation)<br>Lowers cholesterol (maintenance of body functions)<br>Helps form cementing substances (e.g. collagen) that hold body cells together, thus strengthening blood vessels and hastening healing of wounds and bones<br>Increases resistance to infections |
| Vitamin D[1] Vitamin D3 | Boosts immune system (in relation to colds, etc.)<br>Properly utilizes calcium necessary for strong bones and teeth<br>Helps body absorb calcium |
| Vitamin E[1] d-alpha tocopherol | Boosts immune system (in relation to colds, etc.)<br>Relieves muscular cramps (maintains good circulation)<br>Protects against air pollution and other toxic substances |
| succinate | Protects against neuralgic disorders<br>Active in maintaining the involuntary nervous system, vascular system, and involuntary muscles |

[1]Signifies Council for Responsible Nutrition (CRN) List of Dietary Supplemental Ingredients Grandfathered under the Dietary Supplement Health Education Act (DSHEA) September 1998

TABLE 2

JET LAG BEVERAGE MINERALS

| Minerals | Health Benefits as They Relate to Jet Lag Symptoms |
|---|---|
| Zinc[1] zinc picolinate | Boosts immune system (in relation to colds, etc.)<br>Useful in preventing and treating colds<br>Required for maintenance of taste, smell and vision<br>Plays an important role in the formation of protein in the body, thus assists in wound healing, blood formation, and general growth and maintenance of all tissues<br>Aids in the prevention of blindness |
| Selenium[1] | Boosts immune system (in relation to colds, etc.)<br>Capable of detoxifying heavy metals, various drugs, alcohol, cigarette smoke, and peroxidized fats<br>Works in conjunction with vitamin E to protect cells from destruction<br>Promote healing of cold sores and shingles<br>Protect against heart attack and stroke<br>Has anti-inflammatory properties<br>Protective against heart and circulatory disease<br>Works w/vitamin E to protect against oxidation<br>immuno-stimulant |
| Iodine[1] Dulse | Improves mental alertness<br>Promotes healthy hair, nails, skin and teeth |
| Calcium[1] | Aids the nervous system, especially in impulse transmission<br>Aids in muscle contraction, normal nerve functions<br>Relieves cramps in legs<br>Alleviates insomnia (promotes healthy sleep habits)<br>Lowers cholesterol and helps prevent cardiovascular disease<br>Keeps the heart beating regularly<br>Helps metabolize the body's iron (maintenance of body functions)<br>Needed for bone rigidity<br>Helps in blood clotting |
| Iron[1] | Essential for strong immune system<br>Essential for an energetic body and sharp mind<br>Essential for red blood cells to transport oxygen through body, also storage and usage of oxygen<br>Combines with protein in the blood to form hemoglobin (maintenance of body functions) |
| Magnesium[1] magnesium oxide | Vital for a healthy immune system<br>Helps regulate body temperature, muscle contractions, and the nervous system<br>Relieves cramps in legs<br>Helps cells utilize carbohydrates, fats, and proteins<br>Helps in the treatment of high blood pressure<br>Aids in fighting depression<br>Beneficial in the treatment of neuromuscular and nervous disorders |
| Manganese[1] manganese aspartate | Helps eliminate fatigue<br>Reduces nervous irritability<br>Promotes healthy muscle reflexes<br>Necessary for normal development of bones and connective tissues<br>Marginally improves memory |
| Potassium[1] potassium aspartate | Useful in prevention and treatment of high blood pressure<br>Beneficial in the prevention and treatment of cancer<br>Protective against stroke-related death<br>Helps dispose of body wastes<br>May aid in allergy treatment |

TABLE 3

JET LAG BEVERAGE HERBS

| Herbs | Health Benefits as They Relate to Jet Lag Symptoms |
|---|---|
| Chamomile (flower powder)[1] | Relieving stomach distress<br>Calms nerves<br>Fights infection<br>Speeds healing processes<br>Soothes colds |
| Echinacea pallida[1] | Boosts immune system (in relation to colds, etc.)<br>Fights a variety of disease-causing viruses and bacteria<br>Fights infection and strengthens tissues<br>Help the body fight off colds and flu<br>Helps preserve white blood cells<br>Prevents germs from penetrating tissues |
| Echinacea purpurea[1] herb powder and/or root powder | Support the immune system by activating white blood cells<br>Reduce susceptibility to, and duration of colds, flu, and sore throat<br>Fights recurrent respiratory infections such as bronchitis, sinusitis, strep throat, and earache<br>Promoted healing of skin wounds and inflammations, including canker sores, burns, and cuts and scrapes<br>Possibly treat chronic fatigue syndrome<br>Builds immunity during cancer treatments |
| Ginkgo biloba extract[1] | Improvement in blood flow to most tissues and organs<br>Protection against oxidative cell damage from free radicals<br>Block effects of platelet-activating factor (platelet aggregation, blood clotting)<br>Memory enhancement in healthy subjects<br>Relieves altitude sickness |
| Ginseng, American[1] | Boosts immune system<br>Lowers cholesterol |
| Ginseng, Korean[1] panax ginseng | Lowers blood sugars<br>Reduces heart attacks |
| Ginseng, Siberia[1] eleutherococcus senticosus | Protects liver |
| Goldenseal[1] | Relieves indigestion, stomachache, constipation, diarrhea,<br>ulcers, canker sores, sore throat, gingivitis, sore mouth, mild conjunctivitis, colds, flu, and earaches |
| Grape seed extract[1] | Contains oligomeric procyanidins which provide the body<br>with 50 times more antioxidant protection than vitamin C or vitamin E and help prevent and correct damage to capillaries throughout the body<br>Helps relieve poor circulation, including chronic venous insufficiency, varicose veins, macular degeneration, and diabetic retinopathy<br>Increase blood supply to the skin, which helps to prevent the breakdown of collagen<br>Acts as an anti-inflammatory<br>Ability to lower cholesterol and triglyceride levels |

Preferred vitamins to be included in the jet lag beverages of the present invention are listed in Table 4. Preferred minerals to be included in the jet lag beverages of the present invention are listed in Table 5. Preferred herbs to be included in the jet lag beverages of the present invention are listed in Table 6.

TABLE 4

PREFERRED VITAMINS FOR JET LAG BEVERAGES

| Vitamins | USRDA | Preferred Amt. | Acceptable Amt. |
|---|---|---|---|
| Vitamin A (palmitate) | 5,000 IU | 250 IU | 100-5,000 IU |
| Vitamin B1 (thiamin) thiamin HCl | 1.5 mg | 0.2 mg | 0.1-1.5 mg |
| Vitamin B2 (riboflavin) | 1.7 mg | 1.7 mg | 0.425 mg-1.7 mg |
| Vitamin B3 (niacin) | 20 mg | 20 mg | 2-20 mg |
| Vitamin B5 (pantothenic acid) d-calcium pantothenate | 10 mg | 10 mg | 2-10 mg |
| Vitamin B6 (pyridoxine HCl) | 2 mg | 2 mg | 0.5-2 mg |
| Vitamin B12 (cyanocobamamen) | 6 µg | 6 µg | 2-6 µg |
| Vitamin C (ascorbic acid) | 60 mg | 30 mg | 10-60 mg |
| Vitamin D (Vitamin D3) | 400 IU | 20 mg | 4-400 mg |
| Vitamin E (d-alpha tocopherol succinate) | 30 IU | 5 IU | 5-30 IU |

µg = micrograms
IU = international units
mg = milligrams

TABLE 5

PREFERRED MINERALS FOR JET LAG BEVERAGES

| Minerals | USRDA | Preferred Amt. | Acceptable Amt. |
|---|---|---|---|
| Zinc (zinc picolinate) | 9 mg/women<br>11 mg/men | 0.9 mg | 0.5-9 mg |
| Selenium | 55 µg | 24 µg | 15-55 µg |
| Calcium | 1000 mg | 100 mg | 20-200 mg |
| Iodine (Dulse) | 150 µg | 37.5 µg | 20-300 µg |
| Iron | 15 mg/women<br>10 mg/men | 1 mg | 0.75-10 mg |
| Magnesium (magnesium oxide) | 400 mg | 7.5 mg | 5-50 mg |
| Manganese (manganese aspartate) | 2 mg | 2 mg | 1-5 mg |
| Potassium (Potassium aspartate) | No USRDA | 5 mg | 2-20 mg |

TABLE 6

PREFERRED HERBS FOR JET LAG BEVERAGES

| Herbs | Preferred Amt. | Acceptable Amt. |
|---|---|---|
| Echinacea pallida | 50 mg | 10-200 mg |
| Echinacea purpurea (herb powder) | 50 mg | 10-200 mg |
| Ginkgo biloba extract | 50 mg | 5-100 mg |
| Ginseng, Korean (panax ginseng) | 25 mg | 5-100 mg |
| Ginseng, Siberia (eleutherococcus senticosus) | 25 mg | 5-100 mg |
| Grape seed extract | 50 mg | 5-100 mg |
| Goldenseal | 27 mg | 10-570 mg |
| Chamomile | 250 mg | 100-500 mg |

In a preferred embodiment, Rooibos (also known as "red tea") is the primary liquid base and is combined with vitamins, minerals and herbs for the sole purpose of enabling the human body to function normally, by enabling relief of jet lag symptoms via a beverage, and commercially marketed, and/or sold as such.

Referring to Table 4, the beverages of the present invention for preventing or minimizing symptoms of jet lag preferably include at a minimum one vitamin, acceptably two vitamins, most preferably at least four vitamins of which at least three vitamins are B vitamins, and as many as all vitamins, as ingredients for the purpose of enabling the human body to function normally, during and after a flight of at least three hours.

Referring to Table 5, the beverages of the present invention for preventing or minimizing symptoms of jet lag preferably include at least four minerals including zinc, calcium, magnesium and manganese, and may include as many as all vitamins, as ingredients for the purpose of enabling the human body to function normally during and after a flight of at least three hours.

Referring to Table 6, the beverages of the present invention for preventing or minimizing symptoms of jet lag preferably include at least two herbs as ingredients for the purpose of enabling the human body to function normally during and after a flight of at least three hours.

Alternatively, the beverages of the present invention for preventing or minimizing symptoms of jet lag preferably include at least one vitamin from Table 4, at least one mineral from Table 5, and at least one herb from Table 6. More preferably, the beverages of the present invention for preventing or minimizing symptoms of jet lag include at least two vitamins from Table 4, at least two minerals from Table 5, and at least two herbs from Table 6. Even more preferably, the beverages of the present invention for preventing or minimizing symptoms of jet lag include at least three vitamins from Table 4, at least three minerals from Table 5 and at least three herbs from Table 6. Most preferably, the beverages of the present invention for preventing or minimizing symptoms of jet lag includes at least four vitamins from Table 4, at least four minerals from Table 5, and at least four herbs from Table 6.

In less preferred embodiments, the beverages of the present invention for preventing or minimizing symptoms of jet lag contain at least three vitamins from Table 4, and at least three herbs from Table 6. Alternatively, the beverages of the present invention for preventing or minimizing symptoms of jet lag contain at least three minerals from Table 5, and at least three herbs from Table 6.

The foregoing description is considered as illustrative only of the principles of the invention. Further, since numerous modifications and changes will be readily apparent to those skilled in the art, it is not desired to limit the invention to the exact construction and process shown as described above. Accordingly, all suitable modifications and equivalents may be resorted to falling within the scope of the invention as defined by the claims that follow.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

The invention claimed is:

1. A method of reducing jet lag symptoms, comprising: ingesting at least 8 fluid ounces of a beverage comprising vitamin B3; vitamin B5; vitamin B12; vitamin D; calcium; iodine; potassium; magnesium; manganese; ginseng; ginkgo biloba, grape seed extract; and water, during a period of from one hour before a flight, during a flight, or both;
    wherein for each 8 fluid ounces of the beverage, the beverage comprises at least 20 mg of vitamin B3, at least 10 mg of vitamin B5, at least 6 µg of vitamin B12, at least 20 mg of vitamin D, at least 100 mg of calcium, at least 37.5 µg of iodine, at least 5 µg of potassium, at least 7.5 mg of magnesium, at least 2 mg of manganese, at least 50 mg of ginseng, at least 50 mg of ginkgo biloba, and at least 50 mg of grape seed extract.

2. The method of claim 1, wherein at least 8 fluid ounces of the beverage are consumed by an air traveler during a flight of at least 3 hours.

3. The method of claim 1, wherein at least 8 ounces of the beverage are additionally consumed by an air traveler in the last hour of the flight.

4. The method of claim 1, wherein at least 8 ounces of the beverage are additionally consumed by an air traveler after the flight is completed.

5. The method of claim 1, wherein the beverage further comprises *Echinacea* extract.

6. The method of claim 1, wherein the beverage further comprises Vitamin A.

7. The method of claim 1, wherein at least 8 fluid ounces of the beverage are consumed during the first half of the flight.

* * * * *